United States Patent [19]

Podszûn et al.

[11] Patent Number: 4,552,906

[45] Date of Patent: Nov. 12, 1985

[54] POLYMERIZABLE DENTAL COMPOSITIONS AND MOLDED DENTAL ARTICLES PRODUCED THEREFROM

[75] Inventors: Wolfgang Podszûn, Cologne; Fritjof Bley, Achberg; Michael Walkowiak, Leverkusen, all of Fed. Rep. of Germany

[73] Assignee: Bayer Aktiengesellschaft, Leverkusen, Fed. Rep. of Germany

[21] Appl. No.: 605,012

[22] Filed: Apr. 27, 1984

[30] Foreign Application Priority Data

May 7, 1983 [DE] Fed. Rep. of Germany ....... 3316851

[51] Int. Cl.$^4$ ................................................. A61K 6/08
[52] U.S. Cl. .................................. 523/115; 433/199.1; 433/201.1; 433/202.1; 433/228.1; 260/998.11; 523/116
[58] Field of Search ............................. 523/115, 116; 260/998.11; 433/199, 201, 202, 228

[56] References Cited

U.S. PATENT DOCUMENTS

| | | | |
|---|---|---|---|
| 3,629,187 | 12/1971 | Waller | 260/41 R |
| 3,709,866 | 1/1973 | Waller | 523/115 |
| 4,141,144 | 2/1979 | Lustgarten | 32/15 |
| 4,192,940 | 3/1980 | Lindner et al. | 528/370 |
| 4,281,991 | 8/1981 | Michl et al. | 433/202 |

FOREIGN PATENT DOCUMENTS 0014515 8/1980 European Pat. Off. .
0036272 9/1981 European Pat. Off. .

OTHER PUBLICATIONS

Chemical Abstracts, vol. 96, 1982, pp. 338, 339, Abstract 11715v, "Dental Fillings Containing Carbonate Polymers".

Primary Examiner—Lorenzo B. Hayes
Attorney, Agent, or Firm—Sprung Horn Kramer & Woods

[57] ABSTRACT

A dental composition suitable for being polymerized to a dental prosthesis approximately comprising by weight (A) 20 to 50% of a mixture of monofunctional and polyfunctional methacrylic esters and, optionally, other monomers, (B) 20 to 60% of an essentially non-crosslinked polymer homogeneously filled with microfine inorganic filler and based on (meth)acrylic esters and, optionally, other monomers, (C) 0.5 to 25% of a non-crosslinked polymer having a glass transition temperature $\leq 0°$ C. and a molecular weight $M_w$ of $10^3 - 5 \times 10^5$, and (D) 0 to 40% of a finely divided inorganic filler treated with an adhesion promoter.

9 Claims, No Drawings

POLYMERIZABLE DENTAL COMPOSITIONS AND MOLDED DENTAL ARTICLES PRODUCED THEREFROM

The present invention relates to polymerizable compositions for dental purposes which contain a non-crosslinked polymer having a glass transition temperature ≦0° C., and to crosslinked molded dental articles produced from them, in which the non-crosslinked polymer is present as an internal plasticizer resistant to migration.

In particular, the present invention relates to a dental material, specifically a material for producing false teeth, which contains (A) polymerizable methacrylic esters,
(B) a non-crosslinked bead polymer which is homogeneously filled with a microfine inorganic filler,
(C) a non-crosslinked polymer having a glass transition temperature Tg≦0° C., and additionally, where appropriate,
(D) an inorganic filler treated with adhesion promoters.

Customarily, false teeth consist of polymethyl methacrylate (abbreviated to PMMA in the following text). Generally, these teeth are produced by chemoplastic routes using a powder/liquid process, in which a plastic composition comprising a PMMA bead polymer as the powder component and a mixture of methyl methacrylate and ethylene dimethacrylate as the liquid component is cured by radical polymerization while molding.

PMMA teeth have been used successfully for many years, principally because of their physiological compatibility and good cosmetic properties. However, materials which are an improvement on PMMA in respect of important mechanical properties, such as hardness and abrasion resistance, are desirable. Molded dental articles having improved mechanical properties and containing a polymerized, bifunctional dimethacrylate, such as bis-GMA, or a urethane dimethacrylate, in combination with exclusively microfine silicon dioxide as the inorganic filler, are described in DE-AS (German Published Specification) No. 2,462,271. However, false teeth according to DE-AS (German Published Specification) No. 2,462,271 have the technological disadvantage that, on insertion in the prosthesis, they bond less rigidly to the prosthesis base than do customary PMMA teeth.

It is known, from the publication by Hirasawa in "Reports of the Institute for Medical and Dental Engineering", 1968, pages 55–61, that the hardness and abrasion resistance of PMMA can be significantly increased by using microfine silicon dioxide filler. However, materials of this type in the form described are not suitable for use as a dental material because of poor processing properties and, in particular, because they are too brittle.

It has now been found that the mechanical properties of crosslinked molded articles based on polymers of (meth)acrylic esters and filled with 5 to 50% by weight of finely divided inorganic filler can be considerably improved when the molded articles contain 0.5 to 25% by weight, preferably 1 to 10% by weight, of a non-crosslinked polymer having a glass transition temperature ≦0° C. and a molecular weight $M_w$ of $10^3 - 5 \times 10^5$.

In particular, it has been found that a dental material having very good processing properties and improved mechanical properties is obtained by using (A) 20 to 50 parts by weight, preferably 25 to 45 parts by weight, relative to 100 parts by weight of the material, of a polymerizable mixture of monofunctional and polyfunctional methacrylic esters and, where appropriate, acrylic esters and other monomers;

(B) 20 to 60 parts by weight, preferably 25 to 50 parts by weight, of an essentially non-crosslinked polymer homogeneously filled with microfine inorganic filler;

(C) 0.5 to 25 parts by weight, preferably 1 to 10 parts by weight, of a non-crosslinked polymer having a glass transition temperature Tg≦0° C. and a molecular weight $M_w$ of $10^3 - 5 \times 10^5$ and, where appropriate, additionally, (D) up to 40 parts by weight of an inorganic filler treated with adhesion promoters.

The mixture of monofunctional and polyfunctional (meth)acrylic esters (component A) consists, to the extent of 2 to 50% by weight, preferably 5 to 25% by weight, of polyfunctional (meth)acrylic esters as crosslinkers.

Monofunctional methacrylic esters which are primarily suitable are alkyl methacrylates having 1 to 12 C atoms in the alcohol moiety, such as, for example, methyl methacrylate, ethyl methacrylate, i-butyl methacrylate, t-butyl methacrylate, cyclohexyl methacrylate, furfuryl methacrylate, tetrahydrofurfuryl methacrylate, decyl methacrylate and lauryl methacrylate. In particular, mixtures of various methacrylic esters are very suitable, a proportion of more than 50% by weight of methyl methacrylate (relative to the total of monofunctional (meth)acrylic esters employed) being particularly advantageous.

Polyfunctional methacrylic esters are particularly understood to include dimethacrylates and trimethacrylates.

Examples of dimethacrylates which may be mentioned are: neopentylglycol dimethacrylate, 1,12-dodecane dimethacrylate, also derivatives of bisphenol A, such as 2,2-bis-[4(2-hydroxy-3-methacryloyloxypropyl)phenyl]propane (bis-GMA), and urethane dimethacrylate, as are described, for example, in U.S. Pat. Nos. 3,425,988, 3,709,866 and 3,629,187.

Preferred dimethacrylates are ethylene glycol dimethacrylate, diethylene glycol dimethacrylate, triethylene glycol dimethacrylate and butanediol dimethacrylate.

Examples of suitable trimethacrylates are glycerol trimethacrylate, trimethylolpropane trimethacrylate or pentaerythritol trimethacrylate.

In addition to the methacrylates, it is possible to employ up to 20% by weight (relative to the total of component A)) of other vinyl or vinylidene monomers, such as, for example, the acrylates analogous to the abovementioned methacrylates, styrene, α-methylstyrene, acrylonitrile or vinyl acetate.

Component B preferably consists of an essentially non-crosslinked bead polymer having a mean particle size, lightscattering of 20 to 150 μm, preferably 30 to 80 μm, which is homogeneously filled with 10 to 70% by weight, preferably 20 to 50% by weight, of a microfine surface-treated inorganic filler. Any desired (meth)acrylic esters or proportions (up to 20% by weight relative to bead polymer) of other monomers of the abovementioned type are suitable for producing the bead polymer, but compounds essentially having only one olefinic group are employed so that the bead polymer is essentially non-crosslinked and can be at least incipiently dissolved by (meth)acrylic esters. The viscosity of the monomer (mixture) used for producing the bead polymer is preferably in the range from 0.001 to 0.09 Pa.s (1-90 cP) at the temperature of dispersion.

The proportion of component B in the polymer preferably consists of PMMA homopolymer or a copolymer of methyl methacrylate with methacrylic acid or acrylic esters having 2 to 12 C atoms in the alcohol moiety. Examples of copolymers which are particularly preferred comprise 60 to 90% by weight of methyl methacrylate and 40 to 10% by weight of i-butyl methacrylate. The molecular weight ($M_w$) of the polymer is preferably in the range $10^5-5\times 10^6$.

Silicon dioxide is particularly suitable as the microfine inorganic filler (preferred particle size 10 to 500 nm). The silicon dioxide can be prepared, for example, by precipitation or by flame hydrolysis processes. In addition to pure silicon dioxide, it is also possible to employ mixtures of silicon dioxide with, for example, aluminum oxide, boron oxide, titanium dioxide or zirconium oxide, as long as $SiO_2$ is the major proportion in the mixture. Silicon dioxide obtained by flame hydrolysis and having a mean particle size (primary particle size) of 10 to 40 nm and a BET surface area of 30 to 300, preferably 40 to 200, m$^2$/g is particularly well suited.

Suitable surface-treatment agents are primarily the silane compounds which are known per se as adhesion promoters, which are described, for example, in U.S. Pat. Nos. 3,066,113 and 3,539,533. It is possible to use saturated silane compounds, such as, for example, hexamethyldisilazane or γ-glycidoxypropyltrimethoxysilane; however, unsaturated polymerizable silane compounds having vinyl or vinylidene groups are preferably employed, such as vinyltriethoxysilane, vinyltrimethoxysilane, γ-methacryloxypropyltrimethoxysilane, γ-methacryloxypropyl-tris-(2-methoxyethoxy)silane and vinyltriacetoxysilane.

The silane compound should be used in proportions of 1 to 25, preferably 5 to 20, % by weight relative to the microfine filler. The silanizing reaction can be carried out in an inert solvent, for example in methylene chloride or toluene. In some cases, for example in the after-treatment with hexamethyldisilazane, it is also possible to dispense with a solvent. However, it is particularly advantageous to carry out the silanizing reaction in the monomers employed in the suspension polymerization, and to carry out the polymerization immediately with the monomer/filler mixture thus obtained, without isolating the silanized inorganic filler.

Component B is producible by suspension polymerization, for example using a copolymer of methyl methacrylate and methacrylic acid as the dispersing agent, by a process which is not claimed in this patent. The mixture of filler and monomer(s) employed for the suspension polymerization can be produced in customary stirring equipment, preferably using high shear forces (for example stirring energies of 1 to 10 watt/liter. Before polymerization, the mixture is advantageously subjected to a vacuum treatment at 0.01 to 300 torr, preferably 1 to 100 torr (preferably for at least 2 minutes). The vacuum treatment is preferably carried out at room temperature, but it is also possible to use higher or lower temperatures.

Customary monomer-soluble radical formers can be used for the activation. The activated filler/monomer mixture is advantageously added slowly, with stirring, to the aqueous solution of the dispersing agent which has been initially introduced into a reaction vessel, the ratio of monomer phase to water phase being, as a rule, 1:1 to 1:10, preferably 1:2 to 1:5. Thereafter, the polymerization is started by heating to the decomposition temperature of the initiator.

Examples of the non-crosslinked polymers having a glass transition temperature Tg=0° C. which are characteristic for the dental compositions and articles according to the invention are products based on polyurethanes, polycarbonates, polyesters and/or polyethers.

For example, aliphatic polyesters based on $C_4-C_{10}$-dicarboxylic acids and $C_2-C_{10}$-diols, such as polyesters of adipic acid and/or azelaic acid with 1,2-propanediol, 1,3-butanediol, 1,4-butanediol or 1,6-hexanediol, and having a molecular weight greater than 1,000 are well suited. It is possible for the polyesters to have free OH groups as the terminal groups or to be acylated.

Aliphatic polyester and/or polyether carbonates which have repeating structural units of the general formula (I) below are particularly preferred:

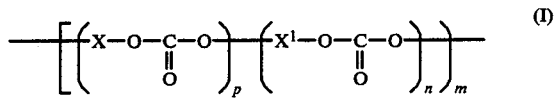

$X^1$ denoting identical or different aliphatic polyester moieties having a molecular weight from 200 to 6,000, preferably from 750 to 3,500, particularly preferably from 1,000 to 2,500, X having the meaning of $X^1$ or representing identical or different aliphatic polyether moieties having a molecular weight from 200 to 20,000, preferably from 700 to 10,000, particularly preferably from 1,000 to 3,000, n being an integer from 0 to 20, p representing an integer from 1 to 20, and m denoting an integer preferably $\geq 20$, the intrinsic viscosity [η] in tetrahydrofuran preferably being 0.5 to 2.5 dl/g, particularly preferably 0.8 to 1.5 dl/g.

Examples of suitable and preferred polyhydric aliphatic alcohols for the polyesters from which the moiety $X^1$ is derived are, where appropriate mixed together, ethylene glycol, 1,2- and 1,3-propylene glycol, 1,4- and 2,3-butylene glycol, 1,6-hexanediol, 1,8-octanediol, neopentyl glycol, cyclohexanedimethanol, 1,4-bis(hydroxymethylcyclohexane), 2-methyl-1,3-propanediol, di-, tri-, tetra- and polyethylene glycol, di-, tri-, tetra- and polypropylene glycol and dibutylene glycol. Mixtures of two of these alcohols are preferred, it being particularly preferred for one of the alcohols to have a branched structure. Examples of these are ethylene glycol/butanediol or hexanediol/neopentyl glycol.

Examples of suitable and preferred polybasic aliphatic carboxylic acids for the polyesters from which the moiety $X^1$ is derived are dibasic aliphatic carboxylic acids, such as carbonic acid, oxalic acid, malonic acid, succinic acid, adipic acid, suberic acid, azelaic acid, sebacic acid, hexahydrophthalic acid, glutaric acid or their mixtures. It is also possible to employ in place of the free carboxylic acids their anhydrides or esters with lower alcohols. Polyesters of adipic acid are preferred.

Examples of suitable lactones for the polyesters from which the moiety $X^1$ is derived are γ-butyrolactone, υ-valerolactone, ε-caprolactone, 6-hydroxyhexanolactone or 8-hydroxyoctanolactone, which can be polyadded onto polyesters in a manner known per se.

Examples of suitable hydroxycarboxylic acids for the polyesters from which the moiety $X^1$ is derived are β-hydroxypropionic acid, γ-hydroxybutyric acid, δ-hydroxyvaleric acid, ε-hydroxycaproic acid, 6-hydroxyhexanoic acid or 4-hydroxycyclohexanecarboxylic acid, which can be condensed to give polyesters in a manner known per se.

Preferred suitable polyether moieties X are those of the general formula (II)

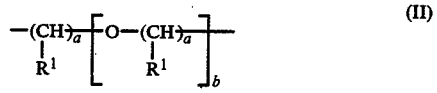

in which the moieties $R^1$ are each identical or different and, independently of one another, denote H or $C_1$-$C_4$-alkyl radicals, preferably H or $CH_3$, a represents an integer from 2 to 10, preferably 2 or 4, and b denotes an integer from 2 to 350, in particular from 3 to 250.

Examples of these are poly(ethylene oxide)glycols, poly(1,2-propylene oxide)glycols, poly(1,3-propylene oxide)glycols, poly(1,2-butylene oxide)glycols, poly(tetrahydrofuran)glycols, the corresponding poly(pentylene oxide)glycols, poly(hexamethylene oxide)glycols, poly(heptamethylene oxide)glycols, poly(octamethylene oxide)glycols, poly(nonamethylene oxide)glycols and the copolymers or block copolymers of, for example, ethylene oxide and propylene oxide. Preferred polyether moieties X are those based on ethylene oxide and/or propylene oxide.

The compounds of the structural formula (I) containing carbonate groups are prepared by reacting the described polyesters and polyethers containing OH terminal groups with bis-aryl esters of carbonic acid of the formula (III)

in which

Ar is a substituted or unsubstituted aryl radical having 6 to 18 C atoms, suitable substituents being, in particular, $C_1$-$C_4$-alkyls, and nitro or halogen groups, or with bis-aryl carbonates of the formula (IV)

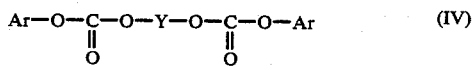

in which Y has the meaning of X and $X^1$ in formula (I) or of a polyester or polyether containing carbonate groups and having the repeating structural unit (I).

The reaction is normally carried out at temperatures from 110° to 200° C. in the presence of transesterification catalysts, such as, for example, alkali metal or alkaline earth metal phenolates, alkali metal or alkaline earth metal alcoholates, tertiary amines, such as, for example, triethylenediamine, morpholine, pyrrolidone, pyridine or triethylamine, or metal compounds, such as antimony trioxide, zinc chloride, titanium tetrachloride and tetrabutyl titanate, the catalyst preferably being employed in amounts between 20 ppm and 200 ppm relative to the total weight of reactants.

Reaction products of this type are known and are described, for example, in DOS (German Published Specification) No. 2,732,718 or in DOS (German Published Specification) No. 2,712,435 and DOS (German Published Specification) No. 2,651,639.

The intrinsic viscosity [$\eta$] is measured in tetrahydrofuran at 25° C. and is recorded in dl/g (for definition, see, for example, H. G. Elias "Makromoleküle" (Macromolecules) published by Hüthig & Wepf, Basel, page 265).

Component D is a finely divided inorganic filler having a mean particle size in the range from 0.01 to 10 $\mu$m which has been treated with adhesion promoters. Examples of suitable inorganic fillers are those which have already been described above as constituents of component B. In addition, it is also possible to employ agglomerated silicas having mean particle sizes of, for example, 0.5 to 10 $\mu$m, or ground glasses or quartz having mean particle sizes in the range of, for example, 1 to 5 $\mu$m. The silane compounds described above are suitable as the adhesion promoters; $\gamma$-methacryloxypropyltrimethoxysilane is particularly preferred. The amount of silane employed is preferably 2 to 25% by weight (relative to component D), the lower figures applying to the coarser fillers and the higher to particularly finely divided fillers. The silanizing reaction can advantageously be carried out in an inert solvent, such as acetone or methylene chloride. A spray-drying process is particularly well suited for isolating the treated filler.

The dental materials and molded dental articles according to the invention can, in addition to the components already mentioned, contain other constituents customarily used in dental materials. Thus, for example, additional non-filled bead polymers known per se can be employed, preferably in amounts up to 15% by weight (relative to the dental composition). It is possible to add known inorganic and organic coloring pigments and opacifying agents in order to adjust the tooth color. It is also possible to use stabilizers and UV absorbers.

The molded dental articles according to the invention are produced by radical polymerization of the dental compositions while molding. Processing is possible both by injection processes and by compression processes, and is generally carried out by the customary methods of producing PMMA teeth, for example by thermal polymerization using polymerization initiators known per se, for example based on peroxides and azo compounds, such as dibenzoyl peroxide, dilauroyl peroxide, cyclohexyl percarbonate and azoisobutyrodinitrile. Mixtures of polymerization initiators having different decomposition temperatures are also well suited.

The molded dental articles according to the invention can be polished to a high gloss. Compared with those based on PMMA, they exhibit markedly improved mechanical properties, in particular a greater hardness and greater abrasion resistance, and an increased Young's modulus. Teeth produced from the material according to the invention can be inserted in prostheses in a conventional manner, an effective and durable bond between tooth and prosthesis base being achieved.

EXAMPLE 1

Preparation of a non-crosslinked bead polymer which is homogeneously filled with microfine inorganic filler.

1.1 Silanizing solution 480 g of $\gamma$-methacryloxypropyltrimethoxysilane, 968 g of deionized water and 144 g of methacrylic acid are mixed at room temperature for 30 minutes, a homogeneous solution being formed.

1.2 Mixture of microfine filler and monomer

The silanizing solution 1.1 is initially introduced together with 3,240 g of methyl methacrylate and 360 g of isobutyl methacrylate into an 8 liter stirred reactor. 2,400 g of microfine silicon dioxide (mean particle size=30 nm, BET surface area=130 m²/g) are added in portions with stirring at high speed (about 400 rpm). The mixture is further stirred at room temperature for 12 hours, the viscosity of the mixture continuously decreasing. The mixture is then treated with a vacuum of 15 torr for 5 minutes, and ventilated with nitrogen.

Immediately before further processing, 24 g of benzoyl peroxide are added to the mixture 1.2, and it is injected into the prepared 40 liter reaction autoclave by increasing the pressure of $N_2$.

1.3 Bead polymer 12.6 kg of distilled water and 5.4 kg of solution of dispersing agent (8.5% aqueous solution, made alkaline with NaOH, of a copolymer of equal parts by weight of methyl methacrylate and methacrylic acid) are initially introduced, while flushing with nitrogen, into a 40 liter autoclave with anchor impeller-stirrer, and are mixed for 5 minutes. With the stirrer running (250 rpm), the mixture of monomers described above (mixture from Example 1.2) is injected in the course of 15 minutes. After addition is complete, the mixture is stirred at room temperature for 2 hours. Then 5 bar of $N_2$ are injected, and the temperature is increased to 80° C. (internal) in the course of 15 minutes. When the exothermic reaction starts (about 30 minutes after heating starts), the mixture is cooled so as to maintain the internal temperature in the range from 80° to 90° C. After the reaction has subsided, the mixture is stirred at 80° C. for 3 hours. After cooling, fines are removed from the solid bead polymer by decanting off, and it is then filtered, washed several times with distilled water and dried at 80° C. 6,000 g of transparent beads having a mean particle diameter of 55 μm and a content of $SiO_2$ of 38% are obtained.

EXAMPLE 2

Dental material according to the invention 10 parts by weight of a polyester containing polycarbonate groups (Example 3 in DE-OS (German Published Specification) 2,732,718) and 0.5 part by weight of dibenzoyl peroxide are dissolved in a mixture of 80 parts by weight of methyl methacrylate and 20 parts by weight of ethylene glycol dimethacrylate.

100 parts by weight of the bead polymer from Example 1 and 60 parts by weight of microfine silanized silicon dioxide (mean primary particle size=30 nm, BET surface area=130 m²/g, silanized with 20% methacryloxypropyltrimethoxysilane) are stirred into this solution, a viscous, slightly tacky composition being produced. By heat treatment at 40° C. for 2 hours, the mixture acquires a plastic, doughy consistency.

The mixture is injection or compression molded and cured in 6 minutes at 130° C.

It will be understood that the specification and examples are illustrative but not limitative of the present invention and that other embodiments within the spirit and scope of the invention will suggest themselves to those skilled in the art.

What is claimed is:

1. In a polymerizable dental composition comprising a polyfunctional (meth)acrylic ester as binder, and about 5 to 50% by weight of a microfine inorganic filler, the improvement which comprises about 0.5 to 25% by weight of a non-crosslinked polymer having a glass transition temperature $\leq 0°$ C. and a molecular weight $M_w$ of about $10^3 - 5 \times 10^5$.

2. A dental composition according to claim 1, comprising by weight
   (A) 20 to 50% of a mixture of monofunctional and polyfunctional methacrylic esters,
   (B) 20 to 60% of an essentially non-crosslinked polymer homogeneously filled with microfine inorganic filler and based on (meth)acrylic esters,
   (C) 0.5 to 25% of a non-crosslinked polymer having a glass transition temperature $\leq 0°$ C. and a molecular weight $M_w$ of $10^3 - 5 \times 10^5$, and
   (D) 0 to 40% of a finely divided inorganic filler treated with an adhesion promoter.

3. A dental composition according to claim 1, wherein the microfine inorganic filler has a particle size of about 10 to 500 nm and a BET surface area of about 30 to 300 m²/g.

4. A dental composition according to claim 1, wherein the microfine inorganic filler comprises silicon dioxide obtained by flame hydrolysis and having a mean particle size of about 10 to 40 nm and a BET surface area of about 40 to 200 m²/g.

5. A dental composition according to claim 1, wherein the microfine inorganic filler is silanized.

6. A dental composition according to claim 1, wherein the non-crosslinked polymer is an aliphatic polyester having a molecular weight of about $10^3 - 5 \times 10^5$.

7. A dental composition according to claim 1, wherein the non-crosslinked polymer comprises a polyester(ether)carbonate having repeating structural units of the formula

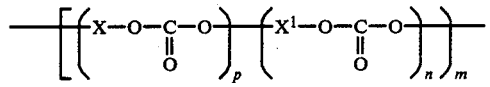

in which
X¹ denotes identical or different aliphatic polyester moieties having a molecular weight from about 200 to 6,000,
X has the meaning of X¹ or represents identical or different aliphatic polyether moieties having a molecular weight from about 200 to 20,000,
n is an integer from 0 to 20,
p is an integer from 1 to 20, and
m $\geq 20$,
the intrinsic viscosity of the polymer in tetrahydrofuran being about 0.5 to 2.5 dl/g.

8. A dental composition according to claim 7, in which
X¹ denotes identical or different aliphatic polyester moieties having a molecular weight from about 750 to 3,500,
X has the meaning of X¹ or represents identical or different aliphatic polyether moieties having a molecular weight from about 700 to 10,000,
n is an integer from 10 to 20, and
p is an integer from 10 to 20.

9. A dental composition according to claim 8, in which
X¹ denotes identical or different aliphatic polyester moieties having a molecular weight from about 1,000 to 2,500, and
X has the meaning of X¹ or represents identical or different aliphatic polyether moieties having a molecular weight from about 1,000 to 3,000.

* * * * *